(12) United States Patent
Nagasawa

(10) Patent No.: US 6,686,336 B2
(45) Date of Patent: Feb. 3, 2004

(54) N-TERMINAL D(-)-PENICILLAMINE PEPTIDES AS ALDEHYDE SEQUESTRATION AGENTS

(75) Inventor: Herbert T. Nagasawa, Richfield, MN (US)

(73) Assignee: Federal Government as represented by the Department of Veterans Affaires, Minneapolis, MN (US)

( * ) Notice: Subject to any disclaimer, the term of this patent is extended or adjusted under 35 U.S.C. 154(b) by 6 days.

(21) Appl. No.: 09/746,555

(22) Filed: Dec. 22, 2000

(65) Prior Publication Data

US 2001/0041789 A1 Nov. 15, 2001

Related U.S. Application Data

(60) Provisional application No. 60/181,060, filed on Feb. 8, 2000.

(51) Int. Cl.$^7$ .................................................. C07K 5/06
(52) U.S. Cl. ..................... 514/19; 530/329; 530/330; 530/331; 514/18; 562/558
(58) Field of Search ................. 530/330, 331, 530/329; 514/19; 562/558

(56) References Cited

U.S. PATENT DOCUMENTS

| | | | |
|---|---|---|---|
| 3,926,736 A | 12/1975 | Bucolo | 435/26 |
| 5,106,834 A | 4/1992 | Bovy et al. | 514/15 |
| 5,112,741 A | 5/1992 | Palmer et al. | 435/25 |
| 5,202,354 A | 4/1993 | Matsuoka et al. | 514/562 |
| 5,525,481 A | 6/1996 | Kaufman et al. | 435/26 |

FOREIGN PATENT DOCUMENTS

| | | |
|---|---|---|
| WO | 93/10747 | 6/1993 |
| WO | 99/03879 | 1/1999 |

OTHER PUBLICATIONS

"L- and D-Pencillamine Hydrochlorides", In: *Biochemical Preparations*, Biochemical Preparations, Inc., pp. 111–118, (1953).
Alexander, C.S., et al., "Lowering of Blood Acetaldehyde Levels—A Possible Approach to Prevention of Alcoholic Cardiomyopathy", *Recent Advances in Studies on Cardiac Structure and Metabolism, vol. 12, Cardiac Adaptation*, pp. 345–350, (1978).
Aschwanden, C., "The smell of age", *Modern Drug Discovery*, p. 58, (Sep.).
Cohen, J.F., et al., "N–Terminal Dipeptides of D(–)–Penicillamine as Sequestering Agents for Acetaldehyde", *Journal of Medicinal Chemistry*, pp. 5 p., (1999).
Goldstein, J.L., et al., "Nonfarnesylated Tetrapeptide Inhibitors of Protein Farnesyltransferase", *The Journal of Biological Chemistry, 266*, 15575–15578, (1991).

Magnier, M., "It Stinks: The Smell of Aging", *Los Angeles Times*, p. 60–62, (Jul. 14, 1999).
Nagasawa, H.T., et al., "2,5, 5–Trimethylthiazolidine–4–carboxylic Acid, a D(–)–Penicillamine–Directed Pseudometabolite of Ethanol. Detoxication Mechanism for Acetaldehyde", *Journal of Medicinal Chemistry*, pp. 1274–1279, (Dec. 1978).
Nagasawa, H.T., et al., "Beta–Substituted Cysteines as Sequestering Agents for Ethanol–Derived Acetaldehyde", *J. Med. Chem., 30*, 1373–1378, (1987).
Nagasawa, H.T., et al., "Chapter 3: Alcoholism: Aldehyde Dehydrogenase Inhibitors as Alcohol Deterrent Agents", In: *Biomedical Chemistry: Applying Chemical Principles to the Understanding and Treatment of Disease*, P.F. Torrence, Ed., Wiley–Interscience, pp. 73–97, (2000).
Nagasawa, H.T., et al., "Lowering of Blood Acetaldehyde Levels as a Therapertic Approach to Alcoholism ", *Alcohol and Aledehyde Metabolizing Systems*, vol. II, Thurman, RG., et al., Eds., Academic Press, New York, pp. 529–536, (1978).
Nagasawa, H.T., et al., "Structural Requirements for the Sequestration of Metabolically Generated Acetaldehyde", *J.Med. Chem., 23*, pp. 140–143, (1980).
Roskoski, Jr., R., et al., "Role of the Carboxyterminal Residue in Peptide Binding to Protein Farnesyltransferase and Protein Geranylgeranyltransferase", *Archives of Biochemistry and Biochemistry and Biophysics, 356*, 167–176, (1998).
Takeshita, T., et al., "Accumulation of Hemoglobin–Associated Acetaldehyde With Habitual Alcohol Drinking in the Atypical ALDH2 Genotype", *Alcoholism: CLinical and Experimental Research, 24 (1)*, pp. 51–57, (Jan. 2000).
Vakevainen, S., et al., "High Salivary Acetaldehyde After a Moderate Dose of Alcohol in ALDH2–Deficient Subjects: Strong Evidence for the Local Carcinogenic Action of Acetaldehyde", *Alcoholism: Clinical and Experimental Research, 24 (6)*, pp. 873–877, (Jun. 2000).

*Primary Examiner*—Christopher S. F. Low
*Assistant Examiner*—David Lukton
(74) *Attorney, Agent, or Firm*—Schwegman, Lundberg, Woessner & Kluth, P.A.

(57) ABSTRACT

The invention provides a compound of formula I:

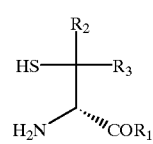

wherein $R_1$–$R_3$ have any of the values described in the specification; or a salt thereof. The compounds are useful as aldehyde sequestration agents (e.g., in the treatment of alcohol-related diseases). The invention also provides compositions comprising such compounds as well as therapeutic methods comprising their administration.

22 Claims, 5 Drawing Sheets

1

2

3

H₂NCRR'CO₂tBu
4

5a, b, c 6a, b, c a    R=R'=H,
b    R=H, R'=i-Pro,
c    R=R'=CH₃

6d

N-TERMINAL D(-)-PENICILLAMINE PEPTIDES AS ALDEHYDE SEQUESTRATION AGENTS

PRIORITY OF INVENTION

This application claims priority from U.S. Provisional Application No. 60/181,060, filed Feb. 8, 2000.

GOVERNMENT FUNDING

The invention described herein was made with government support by the Department of Veterans Affairs. The United States Government has certain rights in the invention.

BACKGROUND

The metabolism of low molecular weight primary alcohols, such as methanol and ethanol, produces aldehydes which are toxic to mammals. When ethanol is metabolized, for example, acetaldehyde (AcH) is produced. Similar to many other aldehydes that are present in the environment or produced by metabolism of an alcohol, acetaldehyde is a toxic compound that may play an etiologic role in the initiation of alcoholic liver disease (ALD), as well as in ethanol-associated digestive cancers in Asian populations with low activity aldehyde dehydrogenase 2 (ALDH-2). Chronic alcoholics have higher blood AcH levels compared to non-alcoholics after consuming alcoholic beverages and are, therefore, more susceptible to its toxic effects. It is now well-established that this ethanol-derived AcH binds covalently to cellular proteins and such AcH modified proteins can elicit an immune response manifested by formation of antibodies to these AcH-bound epitopes. In rodents treated with ethanol, AcH binds to hemoglobin and other plasma proteins, to tubulin, and to a specific cystolic liver protein, as well as to liver collagen. AcH-protein conjugates of hemoglobin have also been detected in humans after consumption of alcohol.

Based on the premise that AcH may play an etiologic role in alcohol-related diseases, the development of AcH sequestration agents has been pioneered. Structure-activity studies suggest that the ideal AcH sequestering agent should have an acidic functional group to impart water solubility, and 1,2- or 1,3-disubstitution with functional groups such as sulfhydryl, amino, or hydroxyl. Of the trifunctional compounds tested that met these requirements, only β-mercapto-α-amino acids with one or two substituents at the β-position were effective in sequestering AcH in vivo. Thus, as depicted in FIG. 1, D(-)-penicillamine (1) and β,β-tetramethylene-DL-cysteine (2) were found to be the best β-mercapto-α-amino acid sequestration agents for AcH in vivo (see Nagasawa et al., *J. Med. Chem,* 1987, 1373–1378).

Although 1 is used clinically to treat Wilson's disease and hereditary cystinuria and to treat rheumatoid arthritis refractory to conventional therapy, its potential for renal and hematological toxicity limits its usefulness as a sequestration agent for AcH. Accordingly, there continues to be a need for aldehyde sequestering agents. Such agents may preferably have improved properties (e.g., reduced toxicity compared to existing agents). There is also a need for pharmacological tools for the further study of the physiological processes associated with alcohol-related diseases and ambient exposure to toxic alcohols and aldehydes.

SUMMARY OF THE INVENTION

These and other needs are met by the present invention which provides aldehyde sequestering agents. Accordingly there is provided a compound of the invention which is a compound of formula I:

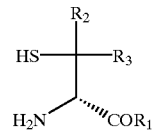

wherein
$R_1$ is an amino acid or peptide; and
$R_2$ and $R_3$ are each independently, hydrogen, $(C_1-C_6)$ alkyl, $(C_3-C_6)$cycloalkyl, or $(C_3-C_6)$cycloalkyl $(C_1-C_6)$alkyl; or $R_2$ and $R_3$ together with the carbon to which they are attached form a 3, 4, 5, or 6-membered carbocyclic or heterocyclic ring, optionally substituted on carbon with $(C_1-C_6)$alkyl, $(C_1-C_6)$haloalkyl, $(C_3-C_6)$cycloalkyl, $(C_3-C_6)$cycloalkyl$(C_1-C_6)$alkyl, $(C_1-C_6)$alkoxy, or $(C_3-C_6)$cycloalkyl$(C_1-C_6)$alkoxy;
or a salt thereof,
provided $R_2$ and $R_3$ are not both hydrogen.

The invention also provides synthetic intermediates useful for preparing a compound of formula I. Accordingly, the invention also provides a compound of formula II:

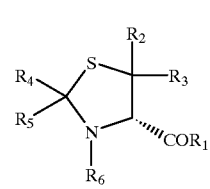

wherein
$R_1$ is an amino acid or peptide;
$R_2$ and $R_3$ are each independently, hydrogen, $(C_1-C_6)$ alkyl, $(C_3-C_6)$cycloalkyl, or $(C_3-C_6)$cycloalkyl $(C_1-C_6)$alkyl; or $R_2$ and $R_3$ together with the carbon to which they are attached form a 3, 4, 5, or 6-membered carbocyclic or heterocyclic ring, optionally substituted on carbon with $(C_1-C_6)$alkyl, $(C_1-C_6)$haloalkyl, $(C_3-C_6)$cycloalkyl, $(C_3-C_6)$cycloalkyl$(C_1-C_6)$alkyl, $(C_1-C_6)$alkoxy, or $(C_3-C_6)$cycloalkyl$(C_1-C_6)$alkoxy, provided $R_2$ and $R_3$ are not each hydrogen;
$R_4$ and $R_5$ are each independently hydrogen, $(C_1-C_6)$ alkyl, $(C_3-C_6)$cycloalkyl, or $(C_3-C_6)$cycloalkyl$(C_1-C_6)$ alkyl; or $R_4$ and $R_5$ together with the carbon to which they are attached form a 3, 4, 5, or 6-membered carbocyclic or heterocyclic ring, optionally substituted on carbon with $(C_1-C_6)$alkyl, $(C_1-C_6)$haloalkyl, $(C_3-C_6)$cycloalkyl, $(C_3-C_6)$cycloalkyl$(C_1-C_6)$alkyl, $(C_1-C_6)$alkoxy, or $(C_3-C_6)$cycloalkyl$(C_1-C_6)$alkoxy; and
$R_6$ is $R_a$—C=O—), wherein $R_a$ hydrogen, $(C_1-C_6)$alkyl, $(C_3-C_6)$cycloalkyl, $(C_3-C_6)$(cycloalkyl)alkyl, or aryl;
provided $R_4$ and $R_5$ are not both hydrogen.

The invention also provides a composition comprising a compound of formula I, or a salt thereof, in combination with a diluent or carrier.

The invention also provides a therapeutic method for treating toxic exposure to an aldehyde in a mammal, comprising administering to a mammal in need of such therapy, an effective amount of a compound of formula I, or a salt thereof.

The invention also provides a method for controlling body odor associated with the secretion of an aldehyde by a mammal, comprising administering to a mammal in need thereof an effective amount of a compound of formula I, or a salt thereof.

The invention provides a therapeutic method for preventing or treating an alcohol-related disease in a mammal, comprising administering to a mammal in need of such therapy, an effective amount of a compound of formula I, or a salt thereof.

The invention also provides a compound of formula I, or a salt thereof, for use in medical therapy (preferably for use in sequestering toxic aldehydes in vivo in mammals) as well as the use of a compound of formula I, or a salt thereof, for the manufacture of a medicament useful for the treatment of an alcohol related disease in a mammal (e.g. a human).

The invention also provides a method for sequestering aldehydes from an emission stream of a source of air pollution comprising contacting the emission stream with a compound of formula I or a salt thereof.

DETAILED DESCRIPTION OF THE INVENTION

Figure 1:
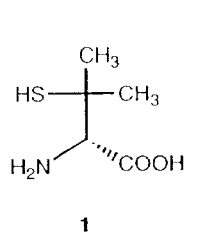
FIG. 1 depicts aldehyde sequestration agents (1 and 2), aldehyde sequestration agents of the invention (6a–d), and useful intermediates (3, 4, and 5).
Figure 1:
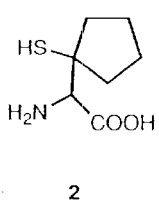
Figure 1:
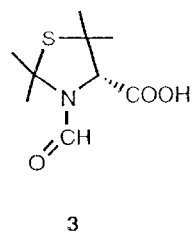
Figure 1:
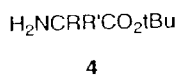
Figure 1:
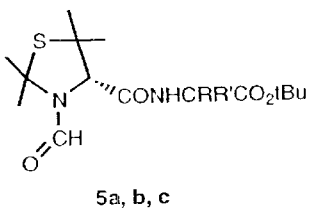
Figure 1:
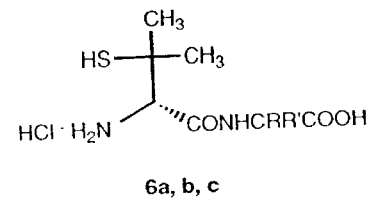
Figure 1:
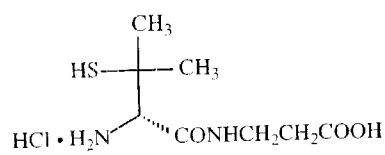

The following definitions are used, unless otherwise described: halo is fluoro, chloro, bromo, or iodo. "Alkyl" denotes both straight chain, cyclic, and branched groups; but reference to an individual radical such as "propyl" embraces only the straight chain radical, a branched chain isomer such as "isopropyl" or cyclic radical such as "cyclopropyl" being specifically referred to.

"Alcohol-related diseases" includes diseases associated with alcohol consumption and metabolism in a mammal. "Alcohol-related toxicities" includes toxicities associated with exposure to alcohol metabolites, such as aldehydes, and aldehyde poisoning. The following non-limiting examples are illustrative. An alcohol-related disease can be a disease related to alcohol abuse, such as cirrhosis of the liver and esophageal cancer. Other alcohol-related diseases may be related to a lack of functional low Km hepatic mitochondrial aldehyde dehydrogenase (AlDH2), a genetic trait inherited by some individuals, many of whom are of Oriental descent. Other alcohol-related diseases are due to toxic exposure to alcohols and aldehydes in the environment or in the workplace. For example, ethylene glycol, which is commonly known and used as antifreeze, is toxic to mammals when it is ingested. As a further example, toxic overexposure to methanol can lead to acidosis and methanol induced blindness. Methanol induced blindness is believed to be due to retinal destruction by formaldehyde, which is an aldehyde metabolite of methanol. Thus, the sequestration agents of the invention can be used to lower the incidence of alcohol-related diseases due to alcohol abuse and prevent methanol induced blindness.

The toxicities of alcohols that are implicated in alcohol-related diseases are generally due to products that are formed from alcohol metabolism. In addition to the metabolism of methanol which gives rise to formaldehyde, the metabolism of ethanol gives rise to acetaldehyde, which can cause an array of health-related problems. The metabolism of ethylene glycol gives rise to glycolaldehyde and glyoxalic acid, and ultimately to oxalic acid, which can cause oxalate poisoning. The metabolism of certain fatty acids gives rise to other, odiferous aldehydes that are secreted in the sweat of some humans. Thus, the aldehyde sequestration agents of the invention can be used to lower the incidence of aldehyde poisoning and to control body odor due to aldehyde secretion.

When a compound of the invention is used to control body odor associated with the secretion of an aldehyde by a mammal, the term "administering to a mammal" includes applying the compound to the skin of the mammal and applying the compound to a garment worn by the mammal, as well as administering the compound orally, or by any other convenient route.

As is well known, many aldehydes are introduced into the working and outdoor environment through the exhaust streams of air pollution emitters. As used herein, an air pollution emitter is any source of air pollution. Air pollution emitter includes stationary and mobile sources of air pollution (See, e.g., Clean Air Act. 42 U.S.C. §7401 et. seq.). For example, acetaldehyde is found in the fuel exhaust of gas- and diesel-powered motor vehicles and machines. Acetaldehyde is thus an air pollutant and ambient exposure to acetaldehyde is a serious public health concern. To that end, "clean alternative fuels" (42 U.S.C. §7581) that are rich in methanol or ethanol emit even greater amounts of aldehydes than conventional fuels. Other aldehydes, such as formaldehyde and glutaraldehyde, are present in medical laboratories and in industrial manufacturing facilities and pose serious health hazards. Thus, the aldehyde sequestration agents can be used to remove aldehydes (e.g., by employing a filter in air purification systems that includes a compound of the invention) from ambient air or emissions from stationary and mobile sources of air pollution such as factories, laboratories, automobiles, and airplanes.

Specific and preferred values for the compounds of the invention are listed below for radicals, substituents, and ranges. The values are for illustration only; they do not exclude other defined values or other values within defined ranges for the radicals and substituents Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl.

A "heterocyclic ring" is a 3, 4, 5, or 6-membered carbocyclic ring comprising an —O—, —S—, or —NR$_x$— in the ring; wherein R$_x$ is hydrogen or $(C_1-C_6)$alkyl.

The term "amino acid," includes the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4-tetrahydroisoquinoline-3-carboxylic acid, penicillamine, ornithine, citruline, α-methyl-alanine, β-alanine, para-benzoylphenylalanine, phenylglycine, propargylglycine, sarcosine, β-alanine, and tert-butylglycine). The term also includes natural and unnatural amino acids bearing a conventional amino protecting group (e.g. acetyl, tert-butyloxy carbonyl, or benzyloxycarbonyl), as well as natural and unnatural amino acids protected at the carboxy terminus (e.g. as a $(C_1-C_6)$ alkyl; or phenyl or benzyl ester or amide. Other suitable amino- and carboxy-protecting groups are known to those skilled in the art (See for example, T. W. Greene, *Protecting Groups In Organic Synthesis;* Wiley: New York, 1981, and references cited therein). An amino acid can be linked to the remainder of a compound of formula I through the N-terminus, or through any other convenient point of attachment The term "peptide" describes a sequence of 2 to 10 amino acids (e.g., as defined hereinabove) or peptidyl residues. The sequence may be linear or cyclic. For example, a cyclic peptide can be prepared or may result from the formation of disulfide bridges between two cysteine residues in a sequence. A peptide can be linked to the remainder of a compound of formula I through the N-terminus, or through any other convenient point of attachment. Preferably a peptide comprises from about 2 to about 10 amino acids, more preferably from about 2 to about 5 amino acids, and most preferably from 2 or 3 amino acids. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right.

A specific value for $R_1$ is an amino acid unprotected at the carboxy terminus.

Another specific value for $R_1$ is a peptide unprotected at the carboxy terminus.

Another specific value for $R_1$ is an amino acid or peptide protected at the carboxy terminus as a $(C_1-C_6)$ alkyl ester, preferably as a t-butyl ester.

Another specific value for $R_1$ is an N-linked amino acid or peptide.

A specific group of compounds of formula I includes compounds wherein $R_2$ is hydrogen and $R_3$ is $(C_1-C_6)$alkyl, $(C_3-C_6)$cycloalkyl, or $(C_3-C_6)$cycloalkyl$(C_1-C_6)$alkyl.

Another specific group of compounds of formula I are compounds wherein $R_2$ and $R_3$ together with the carbon to which they are attached form a 3, 4, 5, or 6-membered carbocyclic ring, optionally substituted on carbon with $(C_1-C_6)$alkyl, $(C_1-C_6)$haloalkyl, $(C_3-C_6)$cycloalkyl, $(C_3-C_6)$cycloalkyl$(C_1-C_6)$alkyl, $(C_1-C_6)$alkoxy, $(C_3-C_6)$cycloalkyl$(C_1-C_6)$alkoxy, provided $R_2$ and $R_3$ are not each hydrogen.

Another specific group of compounds of formula I includes compounds wherein $R_2$ and $R_3$ together with the carbon to which they are attached form a 3, 4, 5, or 6-membered heterocyclic ring, optionally substituted on carbon with $(C_1-C_6)$alkyl, $(C_1-C_6)$haloalkyl, $(C_3-C_6)$cycloalkyl, $(C_3-C_6)$cycloalkyl$(C_1-C_6)$alkyl, $(C_1-C_6)$alkoxy, $(C_3-C_6)$cycloalkyl$(C_1-C_6)$alkoxy.

Another specific compounds of formula I is a compound wherein $R_2$ and $R_3$ together with the carbon to which they are attached form a tetrahydrofuranyl ring, pyrrolidinyl ring, tetrahydrothiofuranyl ring, tetrahydropyranyl ring, piperidinyl ring, or thiopiperidinyl ring.

A preferred group of compounds of formula I are compounds wherein $R_1$ is an amino acid or peptide unprotected at the carboxy terminus and $R_2$ and $R_3$ are each methyl.

Another preferred group of compounds of formula I are compounds wherein $R_1$ is alanine, glycine, valine, or α-amino isobutyric acid.

Another preferred group of compounds are compounds wherein $R_2$ and $R_3$ are each methyl.

Another preferred group of compounds are compounds wherein the carbon atom bearing the group $COR_1$ in a compound of formula I has the (R)-configuration.

Processes for preparing compounds of formula I are provided below as further embodiments of the invention and are illustrated by the procedures provided in which the meanings of the generic radicals are as given above unless otherwise qualified.

A compound of formula I wherein $R_1$ is an amino acid or peptide that is unprotected at the carboxy terminus can be prepared from a corresponding compound of formula I wherein $R_1$ is a protected amino acid or peptide by removal of the protecting group. Accordingly, the invention provides processes for preparing a compound of formula I wherein $R_1$ is an amino acid or peptide that is unprotected at the carboxy terminus comprising deprotecting a corresponding compound of formula I wherein $R_1$ is an amino acid or peptide that is protected at the carboxy terminus.

Additionally, a compound of formula I wherein $R_1$ is an amino acid or peptide that is protected at the carboxy terminus is a useful intermediate for preparing a compound of formula I wherein $R_1$ is an amino acid or peptide that is unprotected at the carboxy terminus.

Figure 2:
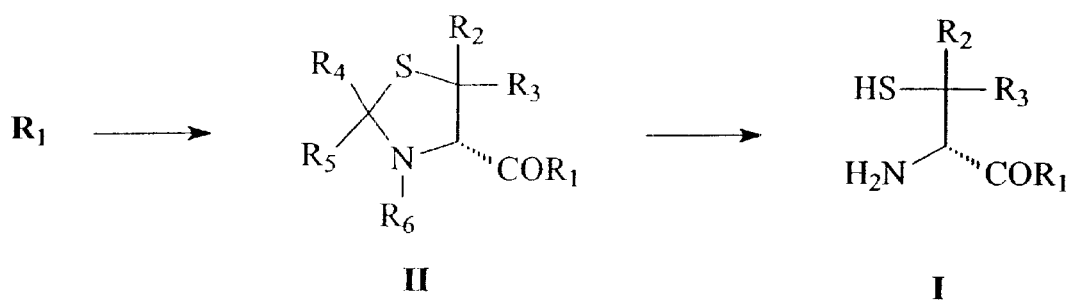
FIG. 2 illustrates the synthesis of compounds of the invention.

Compounds of formula I wherein $R_1$ is β-alanine, glycine, L-valine, or α-amino isobutyric acid can be prepared as outlined in FIG. 2. The t-butyl esters of glycine, L-valine, and α-aminoisobutyric acid (e.g., $R_1$ in FIG. 2) were coupled with the mixed anhydride prepared from 3 and isobutylchloroformate in the presence of $Et_3N$ to give the protected dipeptide esters 5 (FIG. 1), which are compounds of formula II. Simultaneous deformylation, thiazolidine ring opening and de-esterification at the carboxy terminus were readily accomplished by heating compounds of formula II in aqueous acid to give compounds of formula I as their respective ammonium salts. For D-penicillamyl-β-alanine (6d), the coupling procedure was identical to that illustrated in FIG. 2, except ethyl β-alaninate (4d, structure not shown), which is commercially available (see, e.g., the Aldrich Handbook of Fine Chemicals, 2000–2001), was used to prepare the N-protected thiazolidine dipeptide ethyl ester. Deblocking as above gave 6d.

The compounds of formula I can be administered to sequester aldehydes in mammals, such as humans. Aldehyde sequestration may be necessary in order to treat the negative effects due to alcohol ingestion, exposure to ambient alcohols and aldehydes in the environment, and secretion of odiferous aldehydes. In cases where the compounds are sufficiently basic or acidic to form stable nontoxic acid or base salts, administration or use of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, caplettes, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose or other non-reducing sugar, or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, non-reducing sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the desired area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; or by application of a plurality of drops into the eye.

When a compound of formula I is used to sequester ambient aldehydes that have been absorbed through the skin or inhaled, it may be administered by any of the methods disclosed herein.

When a compound of formula I is used to sequester aldehydes from ambient air or from emissions, it can conveniently be immobilized on a suitable inert support, such as cellulose, by physical absorption or by covalent ester linkage to the hydroxyl groups of cellulose through the C-terminal carboxyl group of $R_1$.

When a compound of formula I is used to sequester aldehydes that have been secreted from a mammal (e.g. a human), it can conveniently be applied to the skin of the mammal as part of a topical formulation, or it can be applied to garments worn by the mammal, for example, using an aerosol spray or the like.

The ability of a compound of the invention to sequester aldehydes may be determined using pharmacological models which are well known to the art, or using Tests A or B, described below.

Test A: Sequestration of AcH in a cell-free system.

AcH (40 nmol) was incubated without (control) and with representative compounds of the invention (400 nmol) in a reaction mixture containing 4.0 mM dithiothreitol (DTT) and 40 mM potassium phosphate buffer (pH 7.4) in a total volume of 1.2 ml. The AcH remaining after a 30 minute incubation period at 37° C. was quantified by headspace GC analysis. DTT was included in the reaction mixture to maintain the thiols in their reduced state.

Figure 3:
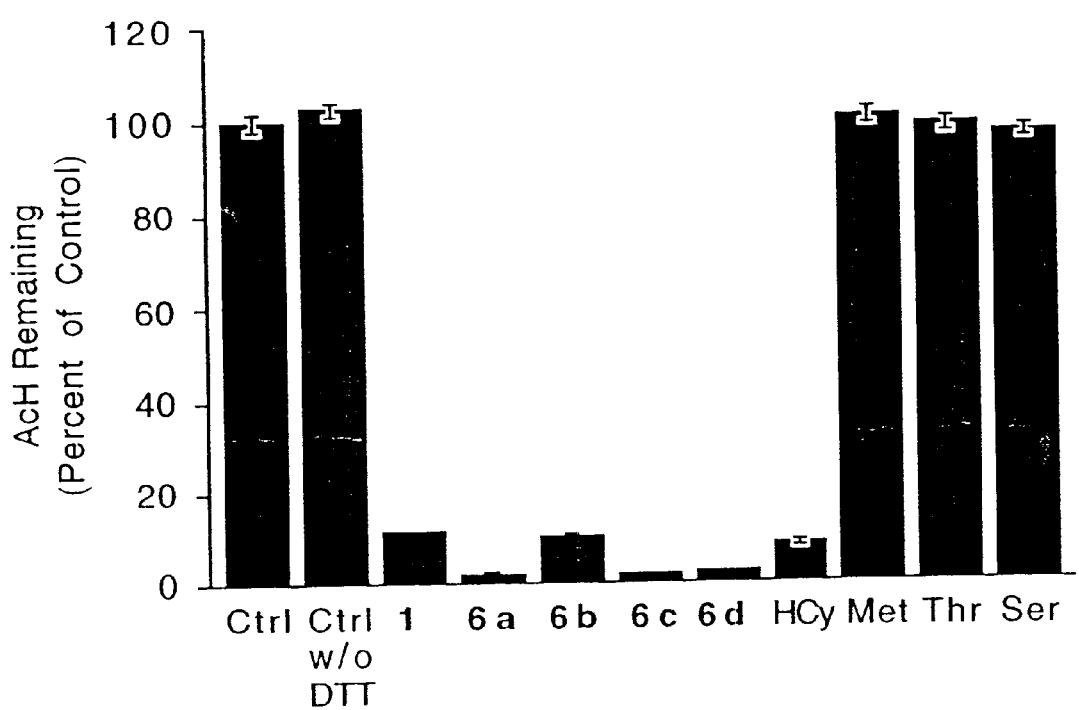
FIG. 3 depicts data for the sequestration of AcH by representative compounds of the invention in a cell-free in vitro system.

The sequestration of AcH by representative N-terminal dipeptides of the invention in a cell-free system is shown in FIG. 3. It can be seen that these dipeptides were equally or more effective than 1 (positive control) in trapping AcH. Methionine (Met), threonine (Thr) and serine (Ser) were totally without AcH sequestering activity. L-Homocysteine (Hcy) was comparable to 1 in sequestering AcH in vitro; however, Hcy was shown not to be an effective AcH-trapping agent in vivo, because Hcy is metabolized too rapidly in vivo.

Test B: Sequestration of AcH in a hepatocyte system.

Hepatocytes from male Wistar rats were isolated and cultured under conditions previously described. On culture day two, ethanol and representative compounds of the invention were added to the culture medium to final concentrations of 20 mM and 1.0 mM, respectively. After 2 hours, 1.0 ml of medium was removed and added to a semicarbazide/sodium azide mixture and frozen until assayed for AcH by gas chromatography. AcH was measured before the addition of ethanol and representative compounds of the invention and 2 hours after incubation, and the values compared against ethanol control without dipeptides. In experiments with cyanamide (to inhibit AlDH), the cyanamide was added with the ethanol to give a final concentration in the culture medium of 50 mM. Results are depicted in FIGS. 4 and 5.

Figure 4:
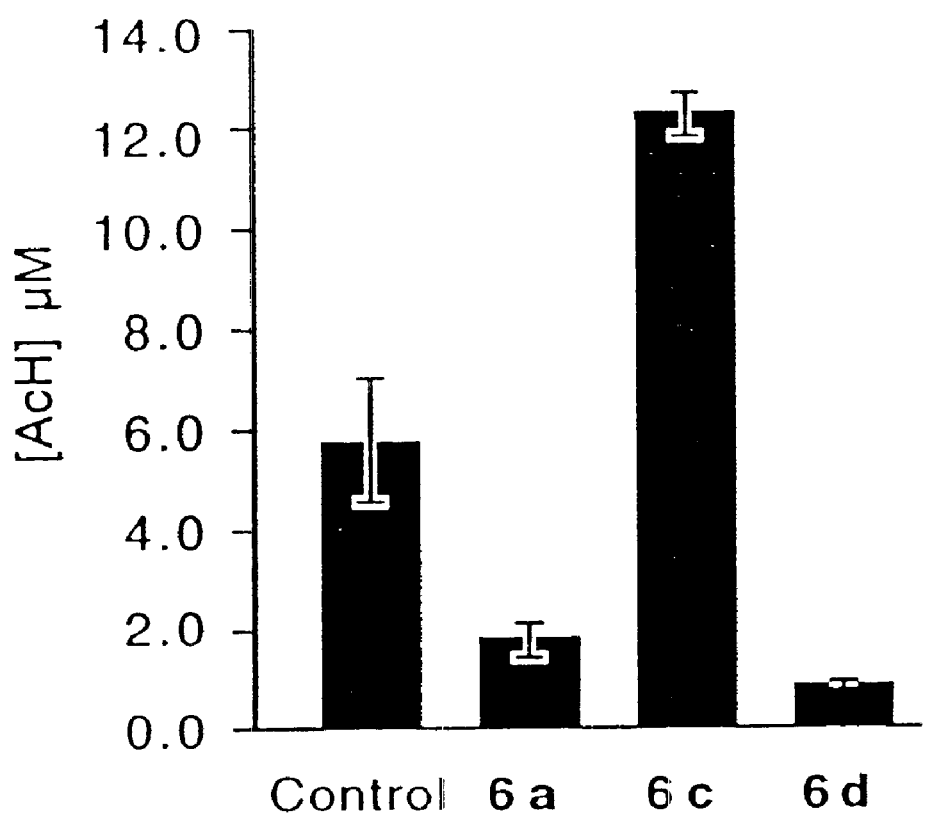
FIG. 4 depicts the effect of representative compounds of the invention on AcH levels at 2 hours in rat hepatocytes.
Figure 5:
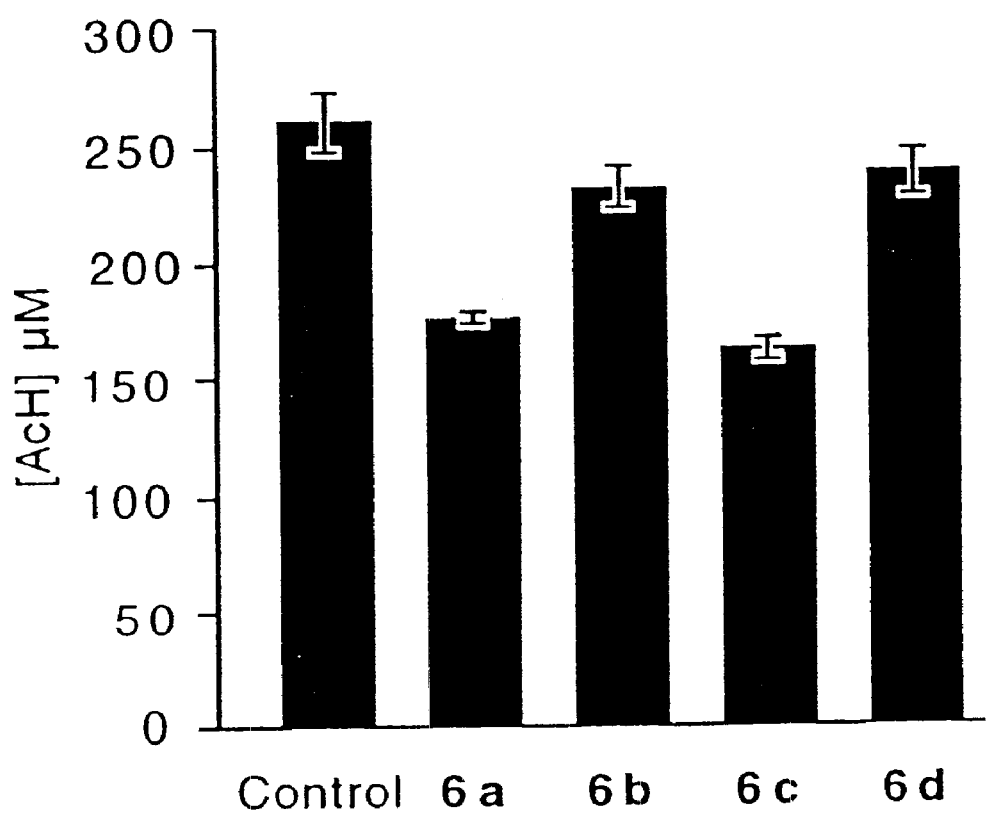
FIG. 5 depicts the effect of representative compounds of the invention on AcH levels at 2 hours in rat hepatocytes incubated in the presence of cyanamide, an inhibitor of AlDH.

In experiments using a hepatocyte culture system, D-penicillamylglycine (6a) and D-penicillamyl-β-alanine (6d), at 1/20 the molar concentration of ethanol (20 mM), lowered the concentration of ethanol-derived AcH by 79 and 84 percent, respectively, at two hrs (FIG. 4). The presence of cyanamide (an inhibitor of AlDH) in the incubation medium resulted in a 45-fold increase in ethanol-derived AcH (FIG. 5, control without dipeptide). Compounds 6a and 6c were able to reduce this concentration by 33 and 37%, respectively. The results suggest that representative compounds of the invention can sequester ethanol-derived AcH.

The invention will now be illustrated by the following non-limiting Examples.

EXAMPLES $^1$H-NMR spectra were recorded at ambient temperature on either a GE-300 or a Bruker AC-200 NMR spectrometer. Chemical shifts are reported as δ values (ppm). Mass spectra (El or FAB) were obtained on a Kratos MS 25 or Finnegan LCQ mass spectrometer. For TLC analyses, Analtech silica gel GF plates were used. The solvent systems used for TLC were as indicated. The plates were visualized by spraying with ninhydrin or ceric sulfate solution and heating. Column chromatography was carried out using columns packed with Kieselgel 60 (230–400 mesh) silica gel (EM Science). A rotating evaporator was used to remove solvents in vacuo.

Example 1

D-Penicillamyl-β-alanine Hydrochloride (6d).

A stirred solution of N-(3-Formyl-2,2,5,5-tetramethylthiazolidine-4S-carbonyl)-βalanine ethyl ester (1.00 g, 3.16 mmol) in 40 ml dioxane: 2 N HCl (1:1) was heated under $N_2$ in a water bath at 85–90° C. An aliquot sampled after 1.75 hours for NMR analysis indicated about 8% starting material remaining. After 3.75 hours, the reaction mixture was evaporated to dryness in vacuo, water was added, and the mixture evaporated to dryness again. NMR analysis indicated about 3% of the formyl group was still uncleaved, although the ester moiety was hydrolyzed. The product was reheated in 15 ml 1 N HCl for an additional 3.25 hours under $N_2$ when NMR analysis indicated the reaction was complete. The solution was lyophilized to give 687 mg (79% yield) of 6d as a hygroscopic solid, mp 71–75° C. $^1$H NMR ($D_2O$): δ 1.32 (s, 3H, $CH_3$), 1.38 (s, 3H, $CH_3$), 2.52

(t, J=6.4 Hz, 2H, CH$_2$CO$_2$H), 3.31, (td, J=6.4 Hz, J=14.0 Hz, 1H, CHNCO), 3.50 (td, J=6.4 Hz, J=14.0 Hz, 1H, CHNCO), 3.78 (s, 1H, CHCS); mass spectrum (FAB), m/z 221 (MH$^+$).

N-(3-Formyl-2,2,5,5-tetramethylthiazolidine-4S-carbonyl)-β-alanine ethyl ester was prepared as follows.

a. N-(3-Formyl-2,2,5,5-tetramethylthiazolidine-4S-carbonyl)-β-alanine ethyl ester To a solution of 3-Formyl-2,2,5,5-tetramethylthiazolidine-4S-carboxylic acid (3) (2.17 g, 10.0 mmol) in 50 ml dry CH$_2$Cl$_2$ was added dry Et$_3$N (2.80 ml, 2.03 g, 20.1 mmol) and the solution was stirred under N$_2$ with ice-bath cooling. To this solution was added isobutyl chloroformate (1.30 ml, 1.37 g, 10.0 mmol) and additional 25 ml of CH$_2$Cl$_2$. The clear solution was stirred about 1 hr and β-alanine ethyl ester hydrochloride (1.56 g, 10.1 mmol) was added. The reaction mixture was allowed to warm to room temperature overnight and was then washed successively with 1N HCl, 5% NaHCO$_3$, and water (50 ml of each). The solution was dried and the solvent evaporated to dryness in vacuo to give 2.89 g of viscous, colorless oil. This was purified by flash chromatography using EtOAc:hexane (1:4, 2:3, and 3:2) as eluent to give 2.12 g (67% yield) of N-(3-Formyl-2,2,5,5-tetramethylthiazolidine-4S-carbonyl)-β-alanine ethyl ester as a colorless oil. $^1$H NMR (CDCl$_3$): d 1.28 (t, J=7.1 Hz, 3H, CH$_3$CH$_2$), 1.42, 1.44, (s, 1:6,3H, CH$_3$CCH),1.64, 1.69, (s, 7:1, 3H, CH$_3$CCH), 1.83, 1.94, (s, 1:5, 3H, CH$_3$CN), 1.97, 1.99 (s, 5:1, 3H, CH$_3$CN), 2.57, (m, 2H, CH$_2$CO$_2$), 3.6, (m, 2H, CH$_2$N), 4.17 (q, J=7.1 Hz, 2H, CH$_2$CH$_3$), 4.34, 4.55 (s, 1:10, 1H, CH), 6.6, (br s, 1H, NH), 8.31, 8.37, (s, 1:10, 1H, HCO); mass spectrum (EI), m/z (rel intensity) 316 (M$^+$, 7), 200 (32), 172 (100), 144 (80).

b. 3-Formyl-2,2,5,5-tetramethylthiazolidine-4S-carboxylic acid (3)

A suspension of 59.7 g (400 mmol) of D(-)-penicillamine in 1200 ml of acetone was heated under reflux with mechanical stirring for 2 hours. The solids were allowed to settle and the supernatant solution was decanted through a filter. The residual solids were heated again in 400 ml of fresh acetone until complete solution resulted (5–10 minutes). The hot solution was poured through the same filter. This process dissolved most of the solids previously held on the filter. Cooling the combined filtrates resulted in the precipitation of a mass of solids which were collected. Concentration (by distillation of the acetone) of the mother liquor followed by cooling gave two additional crops of product giving a total of 68.4 g (90% yield) of 2,2,5,5-tetramethylthiazolidine-4S-carboxylic acid. This was used directly for formylation as described for the racemic compound. Compound 3, obtained in 69% yield, had a mp of 180–181° C. (known 179–180° C. See Leach, B. E., Hunter, J. H. L- and D- Penicillamine hydrochlorides. In *Biochemical Preparations, Vol. 3*; Snell, E. E., Ed; John Wiley & Sons: New York, N.Y., 1953; pp 111–118).

Example 2

D-Penicillamylglycine Hydrochloride (6a)

N-(3-Formyl-2,2,5,5-tetramethylthiazolidine-4S-carbonyl)-glycine t-butyl ester (5a) (931 mg, 2.82 mmol) was hydrolyzed over 10 hours using the same procedure for 6d to give 587 mg of 6a (77% yield) as a hygroscopic solid, mp 67–71° C. $^1$H NMR (D$_2$O): d 1.36 (s, 3H, CH$_3$), 1.44 (s, 3H, CH$_3$), 3.92 (s, 1H, CHCS) 3.92, (d, J=17.8 Hz, 1H, CHNCO), 3.97 (d, J=17.8 Hz, 1H, CHNCO); mass spectrum (FAB), m/z 207 (MH$^+$).

N-(3-Formyl-2,2,5,5-tetramethylthiazolidine-4S-carbonyl)-glycine t-butyl ester was prepared as follows.

a. N-(3-Formyl-2,2,5,5-tetramethylthiazolidine-4S-carbonyl)-glycine t-butyl ester (5a)

To an ice-cooled solution of 3 (5.75 g, 26.5 mmol) and Et$_3$N (7.50 ml, 5.45 g, 53.8 mmol) in CH$_2$Cl$_2$ (80 ml) was added isobutyl chloroformate (3.43 ml, 3.61 g, 26.5 mmol). The milky suspension was stirred for 1 hour and glycine t-butyl ester hydrochloride (4a, 4.44 g, 26.5 mmol) was added. The reaction mixture was stirred with continued cooling for 30 min, then allowed to warm to room temperature overnight and washed successively with 60 ml portions of 1 N HCl, 5% NaHCO$_3$, and H$_2$O. After drying over Na$_2$SO$_4$, the solution was evaporated to dryness in vacuo to give 8.38 g (97% yield) of 5a as an amber oil which slowly crystallized. This product was dissolved in ether (100 ml), diluted with hexane (100 ml), and the solution was evaporated to ca 80 ml and cooled to give 5.19 g (60% yield) of 5a as colorless needles, mp 112.5–113.5° C. $^1$H NMR (CDCl$_3$): d 1.49, 1.50, (s, 3:1, 9H, CH$_3$CO), 1.67,1.72 (s, 7:1, 6H, CH$_3$CCH), 1.96, 1.98, 2.02, (s, 3:3:1, 6H, CH$_3$CN), 3.99, (m, 2H, CH$_2$), 4.4, 4.66, (s, 1:5, 1H, CHCON), 6.5, (br s, 1H, NH), 8.37, 8.41, (s, 1:6, 1H, HCO); mass spectrum (EI), m/z (rel intensity) 330 (M$^+$, 35), 257 (100), 200 (15), 172 (100), 144 (50).

Example 3

D-Penicillamyl-L-valine hydrochloride (6b)

N-(3-Formyl-2,2,5,5-tetramethylthiazolidine-4S-carbonyl)-valine t-butyl ester (5b) (1.07 g, 2.87 mmol) was hydrolyzed for 6 hours using the same procedure for 6d to give, after lyophilization, 780 mg of 6b (96% yield) as a fluffy solid, mp 263–265.5° C. (dec.) $^1$H NMR (D$_2$O): δ 0.84, 0.86 d, 1:1, J=6.8 Hz, 6.8 Hz, 6H, CH$_3$CH), 1.36 (s, 3H, CH$_3$CS), 1.43 (s, 3H, CH$_3$ CS), 2.10, (m, 1H, CHCH$_3$), 3.95, (s, 1H, CHCON), 4.15, 4.16 (d, 1:1, J=5.7 Hz, 5.7 Hz, 1H, CHCO$_2$); mass spectrum (FAB), ml/z 249 (MH$^+$).

N-(3-Formyl-2,2,5,5-tetramethylthiazolidine-4S-carbonyl)-valine t-butyl ester was prepared as follows.

a. N-(3-Formyl-2,2,5,5-tetramethylthiazolidine-4S-carbonyl)-valine t-butyl ester (5b)

5b was prepared as for 5a using 2.17 g (10.0 mmol) of 3 in 30 ml CH$_2$Cl$_2$, Et$_3$N (3.0 ml, 2.78 g, 22.0 mmol), isobutyl chloroformate (1.30 ml, 1.37 g, 10.0 mmol), and 4b (2.10 g, 10.0 mmol). After workup, the reaction mixture was evaporated to approximately 10 ml, diluted with hexane (20 ml) and evaporated to about 10 ml when a mass of colorless needles precipitated, mp 145.5–147° C. A second crop of crystals was obtained by evaporation of the filtrate to approximately 1 ml and dilution with isopentane (5 ml). The total yield of 5b was 2.11 g (57%). $^1$H NMR (CDCl$_3$): δ 0.94, 0.98 (d, 1:1, J=6.8 Hz, 6.8 Hz, 6H, CH$_3$CH), 1.50, 1.51, (s, 2:1, 9H, CH$_3$CO), 1.64, 1.67, 1.73 (s, 8:4:1, 6H, CH$_3$CCH), 1.97, 2.02, (s, 4:1, 6H, CH$_3$CN), 2.20, (m, 1H, CHCH$_3$), 4.4, (m, 1H, CHCO$_2$), 4.66, (s, 1H, CHCON), 6.6, (br d, 1H, NH), 8.36, 8.43, (s, 2:7, 1H, HCO); mass spectrum (EI, m/z (rel intensity) 372 (M$^+$, 65), 316 (100), 200 (100), 172 (100), 144 (100).

Example 4

D-Penicillamyl-α-aminoisobutyric acid hydrochloride (6c)

N-(3-Formyl-2,2,5,5-tetramethylthiazolidine-4S-carbonyl)-α-aminoisobutyric acid t-butyl ester (5c) (192 mg, 0.536 mmol) was hydrolyzed for 5 hours using the same procedure for 6d (except the water bath temperature was 65–70° C.) to give, after lyophilization, 150 mg of 6c (100% yield) as a colorless solid, mp 145–148° C. $^1$H NMR ($D_2O$): δ 1.37, 1.39, 1.448, 1.452 (s, 4:6:3:3, 12H, $CH_3CS$ and $CH_3CCO_2$), 3.79, 3.80 (s, 1:1, 1H, CHCS); mass spectrum (FAB), m/z 235 (MH$^+$).

N-(3-Formyl-2,2,5,5-tetramethylthiazolidine-4S-carbonyl)-α-aminoisobutyric acid t-butyl ester was prepared as follows.

a. N-(3-Formyl-2,2,5,5-tetramethylthiazolidine-4S-carbonyl)-α-aminoisobutyric acid t-butyl ester (5c).

5c was prepared as for 5a using 913 mg (4.20 mmol) of 3 in 50 ml $CH_2Cl_2$, $Et_3N$ (1.2 ml, 0.87 g, 8.6 mmol), isobutyl chloroformate (0.55 ml, 0.58 g, 4.2 mmol), and 4cHCl·0.2$H_2O$ (811 mg, 4.07 mmol). After workup, the $CH_2Cl_2$ solution was evaporated to dryness and the residue was purified by flash chromatography using EtOAc:hexane (1:4) as eluent to give 647 mg (61% yield) of a colorless oil as the byproduct 8. $^1$H NMR ($CDCl_3$): δ0.90, (d, J=6.7 Hz, 6H, $CH_3CH$), 1.44, (s, 9H, $CH_3CO$), 1.49, (s, 6H, $CH_3CN$), 1.88, (m, 1H, $CHCH_3$), 3.80, (d, J=6.7 Hz, 2H, $CH_2CH$), 6.4, (br s, 1H, NH).

Further elution with the same solvent mixture (2:3) gave 407 mg (28% yield) of 5c as a colorless solid. Recrystallization from EtOAc:hexane (1:10) gave an analytical sample, mp 149.5–152° C. $^1$H NMR ($CDCl_3$): δ 1.45, 1.48, (s, 5:1, 9H, $CH_3CO$), 1.54, 1.55, 1.56, 1.62, 1.66 (s, 2:6:6:5:1, 12H, $CH_3CCH$ and $CH_3CCO_2$), 1.91, 1.95, 1.97, (s, 3:3:1, 6H, $CH_3CN$), 4.24, 4.49, (s, 2:7, 1H, CHCON), 6.74, (br s, 1H, NH), 8.37, 8.41, (s, 1:6, 1H, HCO); mass spectrum (EI), mz (rel intensity) 358 (M$^+$, 2), 200 (50), 172 (87), 144 (52).

Example 5

The following illustrate representative pharmaceutical dosage forms, containing a compound of formula I ('Compound X'), for therapeutic or prophylactic use in humans.

| (I) Tablet 1 | mg/tablet |
|---|---|
| 'Compound X' | 100.0 |
| Fructose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Fructose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 ml |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 ml |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

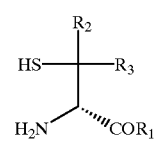

wherein $R_1$ is an amino acid or a peptide of about 2 amino acids to about 5 amino acids; and $R_2$ and $R_3$ are each independently, hydrogen, ($C_1$–$C_6$) alkyl, ($C_3$–$C_6$)cycloalkyl, or ($C_3$–$C_6$)cycloalkyl($C_1$–$C_6$)alkyl; or $R_2$ and $R_3$ together to which the carbon to which they are attached form a 3,4, 5, or 6-membered carbocyolic or heterocyclic ring, optionally substituted on carbon with ($C_1$–$C_6$)alkyl, ($C_1$–$C_6$) haloalkyl, ($C_3$–$C_6$)cycloalkyl, ($C_3$–$C_6$)cycloalkyl ($C_1$–$C_6$)alkyl, ($C_1$–$C_6$)alkoxy, or ($C_3$–$C_6$)cycloalkyl ($C_1$–$C_6$)alkoxy;

or a salt thereof, provided that $R_2$ and $R_3$ are not both hydrogen.

2. The compound of claim 1, wherein $R_1$ is an N-linked amino acid or peptide that is not protected at the carboxy terminus.

3. The compound of claim 1, wherein: $R_2$ and $R_3$ are each independently $(C_1-C_6)$alkyl, $(C_3-C_6)$cycloalkyl, or $(C_3-C_6)$cyclalkyl$(C_1-C_6)$alkyl.

4. The compound of claim 1, wherein $R_2$ and $R_3$ are each methyl.

5. The compound of claim 1, wherein one of $R_2$ or $R_3$ is hydrogen and the other is $(C_1-C_6)$alkyl, $(C_3-C_6)$cycloalkyl, or $(C_3-C_6)$cycloalkyl$(C_1-C_6)$alkyl.

6. The compound of claim 1, wherein $R_2$ and $R_3$ together with the carbon to which they are attached form a cyclopentyl or cyclohexyl ring.

7. The compound of claim 1, wherein $R_2$ and $R_3$ together with the carbon to which they are attached form a tetrahydrofuranyl, tetrahydrothiopyranyl, or pyrrolidinyl ring.

8. The compound of claim 1, wherein $R_2$ and $R_3$ together with the carbon to which they are attached form a tetrahydropyranyl, tetrahydrothiopyranyl, or piperidinyl ring.

9. The compound of claim 1 wherein $R_1$ is a peptide of 2 amino acids or 3 amino acids.

10. The compound of claim 5, wherein $R_1$, is a peptide protected at the carboxy terminus as a $(C_1-C_6)$ alkyl ester.

11. The compound of claim 1, wherein $R_1$, is a peptide protected at the carboxy terminus as a t-butyl ester.

12. The compound of claim 1, wherein $R_1$, is alanine, glycine, valine, or α-aminoisobutyric acid.

13. The compound of claim 1, wherein $R_1$ is alanine, glycine, valine, α-aminoisobutyric acid protected at the carboxy terminus as a t-butyl ester.

14. The compound D-penicillamyl-β-alanine, D-penicillamylglycine, D-penioillaxnyl-L-valine or D-penicillamyl-α-aminoisobutyric acid; or a parmaceutically acceptable salt thereof.

15. A compound of formula II:

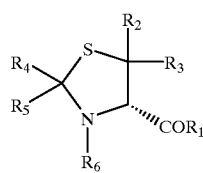

II wherein $R_1$ is an amino acid or peptide of about 2 amino acids to about 5 amino acids;

$R_2$ and $R_3$, are each independently, hydrogen, $(C_1-C_6)$alkyl, $(C_3-C_6)$cycloalkyl, or $(C_3-C_6)$cycloalkyl$(C_1-C_6)$alkyl; or $R_2$ and $R_3$ together with the carbon to which they are attached form a 3, 4,5, or 6-membered carbocyclic or heterocyclic ring, optionally substituted on carbon with $(C_1-C_6)$alkyl, $(C_1-C_6)$haloalkyl, $(C_3-C_6)$cycloalkyl, $(C_3-C_6)$cycloalkyl$(C_1-C_6)$alkyl, $(C_1-C_6)$alkoxy, or $(C_3-C_6)$cycloalkyl$(C_1-C_6)$alkoxy, provided $R_2$ and $R_3$ are not both hydrogen;

$R_4$ and $R_5$ are each independently hydrogen, $(C_1-C_6)$alkl, $(C_3-C_6)$cycloalkyl, or $(C_3-C_6)$cycloalkyl$(C_1-C_6)$alkyl; or $R_4$ and $R_5$ together with the carbon to which they are attached form a 3, 4,5, or 6-membered carbocyclic or heterocyclic ring, optionally substituted on carbon with $(C_1-C_6)$alkyl, $(C_1-C_6)$haloalkyl, $(C_3-C_6)$cycloalkyl, $(C_3-C_6)$cycloalkyl$(C_1-C_6)$alkyl, $(C_1-C_6)$alkoxy, or $(C_3-C_6)$cycloalkyl$(C_1-C_6)$alkoxy, provided $R_4$ and $R_5$ are not both hydrogen; and $R_6$ is $R_a$-C=O-), wherein $R_a$ hydrogen, $(C_1-C_6)$alkyl, $(C_3-C_6)$cycloalkyl, $(C_3-C_6)$cycloalkyl$(C_1-C_6)$alkyl, or aryl.

16. The compound of claim 15, wherein: $R_1$ is an amino acid or peptide protected at the carboxy terminus as a $(C_1-C_6)$alkyl ester; $R_2$ and $R_3$ are each methyl; and $R_4$ and $R_5$ are each methyl.

17. The compound of claim 15, wherein $R_2$ and $R_3$ are each methyl.

18. The compound of claim 15, wherein $R_4$ and $R_5$ are each independently methyl.

19. The compound N-(3-formyl-2,2,5,5-tetramethylthiazolidine-4S-carbonyl)-β-alanine ethyl ester, N-(3-formyl-2,2,5,5-tetramethylthiazolidine-4S-carbonyl)-glycine t-butyl ester, N-(3formyl-2,2,5,5-tetramethylthiazolidine-4S-carbonyl)-valine t-butyl ester, or N-(3-formyl-2,2,5,5-tetramethyltbiazolidine-4S-carbonyl)-α-amino isobutyric acid t-butyl ester.

20. A composition comprising a compound of claim 1, in combination with a diluent or carrier.

21. A method for sequestering aldehydes present in an emission stream comprising contacting the emission stream with a compound of claim 1 for a time and under conditions effective to sequester said aldehydes.

22. A method for sequestering an aldehyde in a mammal exposed to a toxic alcohol or aldehyde, comprising administering to the mammal an effective amount of a compound of claim 1.

* * * * *

UNITED STATES PATENT AND TRADEMARK OFFICE
CERTIFICATE OF CORRECTION

PATENT NO. : 6,686,336 B2
DATED : February 3, 2004
INVENTOR(S) : Nagasawa

It is certified that error appears in the above-identified patent and that said Letters Patent is hereby corrected as shown below:

Title page,
Item [73], Assignee, delete "Affaires" and insert -- affairs --, therefor.
Item [56], References Cited, OTHER PUBLICATIONS, "Nagasawa, H.T., et al.," reference, (4th occurrence), delete "Aledehyde" and insert -- Aldehyde --, therefor.
"Nagasawa, H.T., et al.," (5th occurrence), delete "Biochemistry and" before "Biophysics".
"Takeshita, T., et al.," reference, delete "CLinical" and insert -- Clinical --, therefor.

Column 14,
Line 57, delete "3,4" and insert -- 3, 4 --, therefor.
Line 58, delete "carbocyolic" and inset -- carbocyclic --, therefor.

Column 15,
Line 1, after "wherein" delete ":".
Lines 2-3, delete "$(C_3-C_6)$cyclalkyl$(C_1-C_6)$alkyl" and insert -- $(C_3-C_6)$cycloalkyl$(C_1-C_6)$alkyl --, therefor.
Line 13, delete "tetrahydrothiopyranyl" and insert -- tetrahydrothiofuranyl --, therefor.
Lines 21, 23 and 25 after "$R_1$" delete ",".
Line 31, delete "D-penioillaxnyl-L-valine" and insert -- D-penicillamyl-L-valine, --, therefor.
Line 48, after "$R_3$" delete ",".

Column 16,
Lines 2 and 11, delete "4,5" and insert -- 4, 5 --, therefor.
Line 8, delete "$(C_1-C_6)$alkl" and insert -- $(C_1-C_6)$alkyl --, therefor.
Line 18, delete "$R_a$-C=O-)" and insert -- $R_a$(-C=O-) --, therefor.
Line 22, after "wherein" delete ":".
Lines 33-34, delete "N-(3formyl-2,2,5,5-tetramethylthiazolidine-4S-carbonyl)-valine" and insert -- N-(3-formyl-2,2,5,5-tetramethylthiazolidine-4S-carbonyl)-valine --, therefor.
Lines 35-36, delete "N-(3-formyl-2,2,5,5-tetramethyltbiazolidine-4S-carbonyl)-*a*-amino" and insert -- N-(3-formyl-2,2,5,5-tetramethylthiazolidine-4S-carbonyl)-*a*-amino --, therefor.

UNITED STATES PATENT AND TRADEMARK OFFICE
CERTIFICATE OF CORRECTION

PATENT NO.    : 6,686,336 B2
DATED         : February 3, 2004
INVENTOR(S)   : Nagasawa It is certified that error appears in the above-identified patent and that said Letters Patent is hereby corrected as shown below:

Column 16 (cont'd),
Line 39, after "sequestering" insert -- an --.

Signed and Sealed this

First Day of June, 2004

JON W. DUDAS
*Acting Director of the United States Patent and Trademark Office*